United States Statutory Invention Registration [19]

[11] Reg. Number: H622

Kageyama et al. [43] Published: Apr. 4, 1989

[54] ANALYTICAL ELEMENT FOR MEASURING ACTIVITY OF CREATINE KINASE

[75] Inventors: Shigeki Kageyama; Kazuya Kawasaki; Harumi Katsuyama, all of Saitama, Japan

[73] Assignee: Fuji Photo Film Co., Ltd., Minami-ashigara, Japan

[21] Appl. No.: 195,238

[22] Filed: May 18, 1988

[30] Foreign Application Priority Data

May 18, 1987 [JP] Japan ..... 62-120547

[51] Int. Cl.[4] ..... C12Q 1/54; C12Q 1/50; C12Q 1/48; C12Q 1/32

[52] U.S. Cl. ..... 435/14; 435/15; 435/17; 435/26; 435/805; 422/56

*Primary Examiner*—John F. Terapane
*Assistant Examiner*—J. E. Thomas
*Attorney, Agent, or Firm*—Sughrue, Mion, Zinn, Macpeak & Seas

[57] ABSTRACT

In a dry analytical element for the determination of creatine kinase enzymatic activity is disclosed, comprising at least one porous medium and at least one water permeable layer having a liquid contact relation with the porous medium, the porous medium or the water permeable layer contains creatine phosphoric acid, ADP, a thiol compound as a creatine kinase activation agent, glucose, hexokinase, G6PDH, NAD+, an electron transmission agent and a formazane dye forming tetrazolium salt, the improvement wherein at least one water permeable layer having a liquid contact relation with the porous medium contains a formazane dye forming tetrazolium salt and not more than 16 g/m$^2$ of gelatin.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ANALYTICAL ELEMENT FOR MEASURING ACTIVITY OF CREATINE KINASE

FIELD OF THE INVENTION

The present invention relates to a dry analytical element for use in the quantitative determination of the activity of creatine kinase (hereinafter "CPK") in body liquid, e.g., blood, and a method of manufacturing said element.

BACKGROUND OF THE INVENTION

Various methods have been known for the determination of CPK activity. For example, Japanese Patent Publication No. 9988/71 corresponding to U.S. Pat. No. 3,540,984 discloses a method according to the scheme as shown below, wherein adenosine triphosphate (hereinafter ATP) is formed from CPK using creatine phosphoric acid (hereinafter "CP") and adenosine diphosphate (hereinafter ADP) as substrates. The ATP thus formed is converted into glucose 6-phosphoric acid (hereinafter "G6P") by utilizing glucose and hexokinase. The G6P thus formed is further converted into NADH or NADPH by using nicotinamide adenine dinucleotide (hereinafter NAD+) or nicotinamide adenine dinucleotide phosphate (heinafter) NADP+) and glucose 6-phosphate dehydrogenase (hereinafter "G6PDH"). An increase in NADH or NADPH is optically measured at a wavelength of 340 nm to thereby determine the CPK enzyme activity.

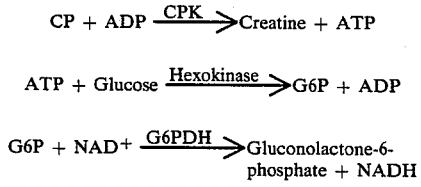

This method is widely known as the SSCC method. This method, however, needs the measurement of light in the ultraviolet region and thus suffers from disadvantages in that the equipment employed is expensive and the measurement is interferred by many compounds having an absorption in the ultraviolet region.

If a colorimetric method is employed wherein a formazane dye, having an absorption spectrum in the visible light region, is derived from the NADH formed by the enzymatic reaction, by utilizing an electron receiving dye precursor and an electron transfer agent, NADH can be quantitatively determined by spectral measurement in the visible light region. This method is described in, for example, Japanese Patent Application (OPI) No. 11395/74 corresponding to U.S. Pat. No. 3,663,374. The term "OPI" as used herein means a "published unexamined patent application".

The quantitative determination in an aqueous solution system needs a complicated procedure and a long amount of time because a series of chemical reactions must proceed in aqueous solution. In view of these problems, a dry analytical element has been developed which does not need a complicated liquid preparation process and which permits a rapid and simplified analysis. In particular, a mono-unit type multi-layer analytical element which is of high analytical accuracy is disclosed in, for example, Japanese Patent Publication No. 21677/78 corresponding to U.S. Pat. No. 3,992,158 and Japanese Patent Application (OPI) No. 164356/80 corresponding to U.S. Pat. No. 4,292,272. An attempt to incorporate the aforementioned reaction system for use in a CPK activity determination into the mono-unit type multi-layer analytical element has been made, as described in Japanese Patent Application (OPI) Nos. 88097/84 and 254199/86 corresponding to U.S. Pat. No. 4,713,327. However, in the storage stability of the above CPK activity determination elements in the summer season or at high temperatures in the tropics is insufficiently low. For example, when allowed to stand at 35° C. for two days or more, the elements produce an error in the measurement of the enzymatic activity and thus are unsuitable for practical use.

SUMMARY OF THE INVENTION

Therefore an object of the present invention is to provide a dry multi-layer analytical element for the determination of CPK activity which makes it possible to measure CPK activity by the use of a spectral photometer in the visible light region, which can stably maintain its performance at higher temperatures than 30° C., and which does not produce a serious error in the determination of enzymatic activity.

The present invention, in an embodiment thereof, provides an improvement wherein at least one water permeable layer contains a formazane dye-forming tetrazolium salt and not more than 16 g/m$^2$, preferably 5 g to 16 g/m$^2$ and most preferably from 10 g/m$^2$ to 16 g/m$^2$, of gelatin, in a dry analytical element for the determination of creatine kinase enzymatic activity, comprising at least one porous medium and at least one water permeable layer having a liquid contact relation with the porous substrate, wherein said porous medium or water permeable layer contains creatine phosphoric acid, ADP, a thiol compound as a creatine kinase activation agent, glucose, hexokinase, G6PDH, NAD+, an electron transmission agent and a fomazane dye-forming tetrazolium salt.

In another embodiment, the present invention provides a dry multi-layer analytical element for the determination of CPK enzymatic activity, comprising at least one porous medium, at least one water permeable layer having a liquid contact relation with said porous medium, and a water impermeable light transmission support laminate in this order, wherein said porous medium or water permeable layer having a liquid contact relation with said porous medium contains creatine phosphoric acid, ADP, a thiol compound as a CPK activation agent, glucose, hexokinase, G6PDH, NAD+ and an electron transmission agent, and at least one of said water permeable layers (having a liquid contact relation with the porous layer) contains not more than 16 g/m$^2$, preferably from 5 g to 16 g/m$^2$ and more preferably from 10 g to 16 g/m$^2$ of gelatin and a formazane dye-forming tetrazolium salt.

DETAILED DESCRIPTION OF THE INVENTION

Even in a dry analytical element for the determination of CPK activity which has a porous medium and in which said porous medium or a water permeable layer having a liquid contact relation with said porous medium contains creatine phosphoric acid, ADP, a thiol compound as a CPK activation agent, glucose, hexokinase, G6PDH, NAD+ and an electron transmission agent, and at least one of said water permeable layers contains a formazane dye-forming tetrazolium salt, if the water permeable layer containing the formazane dye-forming tetrazolium salt is composed of more than 16 g/m$^2$ of gelatin, the element is insufficiently low in storage stability at high temperatures. For example, if it is allowed to stand at 35° C. for a few days, it produces an error in the determination of enzymatic activity and thus is unsuitable for practical use.

The water permeable layer in the present invention is a layer having a property of water permeation, and includes, for example, a reagent layer, a water absorption layer, an adhesive layer, a light shielding layer, a filtration layer, etc. The porous medium in the present invention is porous itself and includes, for example, a spreading layer, etc.

The reagents which are contained in the analytical element of the present invention are creatine phosphoric acid (CP), preferably in amount of 0.1 g to 10 g/m$^2$, and ADP, preferably of 0.1 g to 10 g/m$^2$ as substrates, a thiol compound as an activation agent, glucose, preferably of 0.01 g to 10 g/m$^2$, hexokinase, preferably of $1\times10^3$ to $1\times10^5$ U/m$^2$, G6PDH, preferably of $1\times10^3$ to $1\times10^5$ U/m$^2$, NAD$^+$, preferably of 0.1 g to 10 g/m$^2$, an electron transmission agent, N-acetylcysteine(NAC), preferably of 0.1 g to 10 g/m$^2$, adenosine monophosphate (AMP), preferably of 0.1 g to 10 g/m$^2$ and a formazane dye precursor. Of these compounds, the compounds other than the formazane dye precursor may be contained in the porous medium or the water permeable layer having a liquid contact relation with the porous medium. The reagents or portions thereof may be contained in different layers each other.

As the thiol compound as a CPK activation agent, cysteine, glutathione, reduced form, mercaptoethanol and the like can be used. Of these compounds, N-acetylcysteine (NAC) is preferred. The molar ratio of the thiol compound to ADP is preferably not more than 3.0, more preferably 0.1 to 3.0 and most preferably 0.5 to 1.5.

In the preparation of the dry analytical element for the determination of CPK activity, it is desirable that the thiol compound be added to a coating composition for a layer different from the layer essentially containing the formazane dye precursor. For this purpose, there can be employed a method in which the water permeable layer is obtained by coating with a composition containing the tetrazolium salt, the porous medium layer is obtained by coating with a composition containing the thiol compound, or a preformed layer of the porous medium is obtained by coating with or dipping in the thiol compound-containing composition.

As the electron transmission agent, thiaforase, N-methylphenazinium methosulfate, N-methoxyphenazinium methosulfate and the like can be used. In a case of diaphorase, the electron transmission agent is preferably used in an amount of $1\times10^3$ to $1\times10^5$ U/m$^2$ and more preferably $1\times10^3$ to $4\times10^4$ U/m$^2$.

As the formazane dye precursor, INT, i.e., 2-(p-iodophenyl)-3-(p-nitrophenyl)-5-phenyltetrazolium chloride, BT, i.e., 3,3'-(3,3'-dimethoxy-4,4'-biphenylene)-bis[2,5-diphenyltetrazolium chloride], 3,3'-(4,4'-biphenylene)-bis[2,5-diphenyltetrazolium chloride], and the like can be used. Preferably, nitrotetrazolium blue (NTB or NBT), i.e., 3,3'-(3,3'-dimethoxy-4,4'-biphenylene)-bis[2-(p-nitrophenyl)-5-phenyltetrazolium chloride] can be use. The amount used in the present invention of the formazane dye precursor is preferably from 0.1 g to 3 g/m$^2$ and more preferably from 0.3 g to 1.5 g/m$^2$.

The present invention can be applied to various known dry analytical elements. In particular, it can be applied to an element containing a solid support permeable both to a detecting reagent system and a liquid to be tested. The element may have a multi-layer structure containing as well as the porous medium, a subbing layer, a water absorption layer, an adhesive layer, a reagent layer, a light shielding layer, a filtration layer and other known layers provided on a light transmission liquid impermeable support. Such elements are disclosed in U.S. Pat. No. 3,992,158 and Japanese Patent Application (OPI) No. 164356/80.

The preferable thickness of the porous medium, the water permeable layer, and the support is 100 to 650 μm, respectively.

In the analytical element of the present invention, at least one layer nearest the top surface among the porous medium is preferable a so-called spreading layer which acts to receive a liquid sample and extend it over a suitable surface area, and to diffuse it to another water permeable layer having a liquid contact relation therewith; in particular, a spreading layer having a liquid measuring action. The liquid measuring action means an action that extends a liquid sample spotted to the surface in a nearly constant proportion per unit area in the width (surface) direction with substantially no deviation in the layer. The element may have a porous medium other than the spreading layer.

When a support is used, the dry analytical element of the present invention may have the following structures:

(1) A reagent layer and a spreading layer are provided in this order on a support. A water absorption layer may be sandwiched between the support and the reagent layer.

(2) A second reagent layer, a first reagent layer and a spreading layer are provided in this order on a support. A water absorption layer may be sandwiched between the support and the second reagent layer.

(3) A reagent layer, a light shielding layer and a spreading layer are provided in this order on a support. A water absorption layer may be sandwiched between the support and the reagent layer.

(4) A second reagent layer, a light shielding layer, a first reagent layer and a spreading layer are provided in this order on a support. A water absorption layer may be sandwiched between the support and the second reagent layer.

In (1) to (4) above, a filter layer may be provided between the reagent layer and the spreading layer, or between the second reagent layer and the first reagent layer, or between the light shielding layer and the reagent layer or spreading layer.

In the analytical element for the determination of CPK activity of the present invention, it is preferred that not only the thiol compound but also NAD$^+$ and the electron transmission agent be added to a coating composition different from the coating composition containing the formazane dye forming tetrazolium salt.

As the material constituting the matrix of the spreading layer, filter paper, unwoven fabrics, fabric textures such as plain weaves e.g., broad cloth and poplin; knitted cloth such as tricot; glass fiber filter paper; a membrane filter made of a brush polymer; three dimensional lattice structures made of polymer particles, and the like can be used. Of these, fabric textures and are knitted fabric are preferably used. In detail, Japanese Patent Application Nos. 164356/80, 66359/82 and 222769/85 can be referred to. It is preferred that the fabric texture and knitted fabric be substantially freed of fats and oils attached at the time of preparation, by applying a decreasing treatment such as washing with water.

With regard to the fabric or fabric textures to be used as the spreading layer of the analytical element of the present invention, a physical activation treatment (e.g., glow discharge treatment and corona discharge treatment) disclosed in Japanese Patent Application (OPI) No. 66359/82 can be applied to at least one surface of the fabric, or a hydrophilic polymer dipping treatment disclosed in Japanese Patent Application (OPI) Nos. 164356/80 and 66359/82 can be applied, or a treatment to make such hydrophilic, such as the method disclosed in Japanese Patent Application (OPI) No. 222770/85 can be applied to strengthen the adhesion force between the spreading layer and another layer of the analytical element.

In bonding the spreading layer of fabric or fabric texture to the aforementioned water absorbing layer, detecting layer, reagent layer or adhesion layer, the method disclosed in Japanese Patent Application (OPI) Nos. 164356/80 and 66359/82 can be used. That is, after coating of the water absorbing layer or adhesive layer, the fabric is superposed on a swollen layer and bonded together by applying pressure uniformly and slightly, while the layer is wet, or after the layer is dried and thereafter water (which may contain a small amount of a surfactant) is applied substantially uniformly to swell the layer.

Where the spreading layer is made of a brush polymer or is membrane filter, it can be provided by the method described in, for example, Japanese Patent Publication No. 21677/78, where the spreading layer is a three dimensional lattice structure made of polymer microbeads, it can be provided by the method described in Japanese Patent Application (OPI) No. 90859/80 and where the spreading layer is made of filter paper or unwoven fabric, it can be provided by the method described in, for example, Japanese Patent Application (OPI) No. 148250/82.

Where the hydrophilic polymer binder of the aforementioned detection layer and adhesive layer is gelatin or a gelatin derivative, there can be employed a method in which after coating of the layer, while the gelatin and the like are in the state of a gel, the material constituting the spreading layer is bonded or laminated.

In incorporating reagents such as a substrate, glucose, enzyme, co-enzyme, an activation agent and the like, and if necessary, a hydrophilic polymer, a buffer, a light shielding fine particles and the like in the spreading layer, a coating solution containing the above ingredients can be coated from the top of the spreading layer by known methods. Where the spreading layer is made of fabrics, knitted fabric, filter paper, unwoven fabric and the like, there can also be employed a method in which the spreading layer is dipped in a solution containing the reagents and then dried. Where the spreading layer as described above is laminated, there can be employed a method in which the spreading layer, having been dipped in the manner as described above, is laminated on another layer in the state of either dry or half-dry. Where the spreading layer is a layer formed by coating, for example, a layer made of blush polymer, there may be employed a method in which a solution or dispersion of reagents such as substrate and an enzyme is mixed with the coating solution for the layer and the resulting mixture is coated.

In the analytical element for the determination of CPK activity of the present invention, it is preferred that at least one of CP and ADP as substrates be contained in the spreading layer.

The reagent layer of the analytical element of the present invention is preferably of a continuous phase containing a hydrophilic polymer as the binder. At least one of the reagent layers may be a porous layer as described in connection with the spreading layer. In the reagent layer can be incorporated a hydrophilic polymer a buffer, light reflective fine particles and the like if necessary.

Examples of hydrophilic polymers which can be incorporated in the reagent layer are starch, cellulose, agarose, gelatin and their derivatives (e.g., hydroxymethylated derivatives and hydroxypropylated derivatives), acrylamide polymers, copolymers of acrylamide and various vinyl monomers, polyvinyl alcohol, vinylpyrrolidone polymers, copolymers of vinylpyrrolidone and various vinyl monomers, acrylic acid polymers, copolymers of acrylic acid and various vinyl monomers, and the like. Of the above hydrophilic polymers, gelatin, gelatin derivatives, polyvinyl alcohol, vinylpyrrolidone polymers, acrylamide polymers and cellulose derivatives are preferred.

The analytical element of the present invention contains a formazane dye forming tetrazolium salt in at least one of the reagent layers. This formazane dye forming tetrazolium salt-containing layer contains not more than 16 g/m$^2$, preferably from 5 g to 16 g/m$^2$ and more preferably from 10 g to 16 g/m$^2$ of gelatin. This gelatin may be acid-treated gelatin or alkali-treated gelatin, and further may be subjected to deionization treatment. As part or all of the gelatin, a gelatin derivative, such as phthalated gelatin, can be used.

The reagent layer may contain all of the components of the reagent system or only part of the components. Of the reagent system, CP, ADP, glucose, hexokinase, G6PDH, NAD$^+$, and an electron transmission agent may be contained in the reagent layer, but may be contained in the porous medium, for example, the spreading layer. The layer containing reagents other than the formazane dye forming tetrazolium salt may be a substantially uniform layer containing a hydrophilic polymer as the binder. However, a porous layer as described in, for example, Japanese Patent Application (OPI) Nos. 70163/83, 4959/86, Japanese Patent Application Nos. 256408/85, 279859/85, 279860/85 and 279861/85 can be applied.

Buffers which can be incorporated in the reagent layer are carbonates, borates, phosphates and buffers of Good as described in *Biochemistry,* Vol. 5 (No. 2), pp. 467–477 (1966). This buffer can be selected appropriately referring to, for example, T. Horio et al., *Tanpakushitsu Koso no Kiso Jikken* (Basic Experimental Method for Protein and Enzyme), Nankou-Do, Tokyo, 1981. The reagent layer may further contain light reflective particles as described hereinafter.

The light transmission and water impermeable support is a transparent film usually having a thickness ranging between 50 μm and 500 μm, made of a synthetic or half-synthetic polymer such as polyethylene terephthalate, polycarbonate, polystyrene, cellulose esters (e.g., cellulose triacetate and cellulose acetate propionate) and the like. The adhesion between the support and another layer such as a reagent layer provided in contact with the support can be increased by providing a subbing layer on the surface of the support.

In place of the subbing layer, or simultaneously with application of the subbing layer, the surface of the support may be subjected to physical treatment (e.g., glow discharge and corona discharge) or chemical activation treatment to increase the adhesion force.

In the analytical element of the present invention, a water absorbing layer may be provided on the support; the water absorbing layer may be provided through a layer such as the subbing layer. The water absorbing layer is generally a layer in which the dye formed in the presence of a test sample is substantially prevented from diffusing, and is preferably a layer of a hydrophilic polymer which swells on absorbing water.

The hydrophilic polymer which can be used in the water absorbing layer is generally a natural or synthetic hydrophilic polymer having a rate of swelling of from about 1.5 to 10 at 30° C. Examples of such hydrophilic polymers are agarose, polyacrylamide, polyvinyl alcohol, polyvinyl pyrrolidone. The thickness in the dry state of the water absorbing layer is from 1 μm to 100 μm and preferably from about 3 μm to 30 μm. The water absorbing layer may contain a surfactant (e.g., cationic, amphoteric, nonionic and anionic surfactants) and a buffer, if necessary.

On the layers such as the light-shielding layer, the filtration layer, the reagent layer and the like, an adhesive layer may be provided in order to laminate or bond the spreading layer. The adhesive layer is generally made of a hydrophilic polymer which is able to bond the spreading layer when swelling on absorbing water. As such hydrophilic polymers, the same polymers as used in the water absorbing layer can be used. Of these, gelatin, polyacrylamide and the like are preferred. The dry film thickness of the adhesive layer is generally in the range of from 0.5 to 20 μm.

In the analytical element of the present invention, a light shielding layer can be provided. This light shielding layer is preferably a water permeable layer in which light reflective fine particles are dispersed in a hydrophilic polymer as the binder. These light reflective fine particles, in measuring detectable change (color change, color formation, etc.) developed in, for example, the reagent layer, from the side of the light transmission support, shields the color of an aqueous solution spotted to the spreading layer, particularly the red color of hemoglobin when the sample is blood, and at the same time, acts to a light refelection layer or background layer.

Preferred examples of fine particles capable of reflecting light are fine particles of titanium dioxide and fine particles of barium sulfate. If desired, light refelective fine particles may be incorporated in the liquid spreading layer.

The detecting layer can contain light reflective fine particles, if necessary.

Preferred body fluid containing CK used for determination using the analytical element includes, for example, whole blood, blood plasma, blood serum, lymph, bile, urine, bone marrow fluid, phlegm, sweat, excrement, etc., but not limited thereto.

The present invention is described in greater detail with reference to the following examples, although it is not intended to be limited thereto.

EXAMPLE 1

The surface of a transparent polyethylene terephthalate film (thickness: 180 μm) was subjected to a treatment to make it hydrophilic by coating a diluted gelatin solution, and a coating solution having the formulation shown below was coated thereon and dried to form a color forming layer having a dry film thickness of 10 μm (gelatin coated amount: about 13.3 g/m$^2$).

| Coating Solution for Color Forming Layer: | |
|---|---|
| Gelatin | 100 g |
| Water | 900 g |
| NTB (Nitrotetrazolium Blue) = 3,3'-(3,3'-dimethoxy-4,4'-biphenylene)bis[2-(p-nitrophenyl)-5-phenyltetrazolium chloride)] | 6 g |

The above color forming layer was moistened with about 30 g/cm$^2$ of water and then pressed onto a tricot fabric made of polyethylene terephthalate yarns (36 gage, 50D) to form a spreading layer.

On this spreading layer, a coating solution having the formulation shown below was coated in an amount of 120 ml/m$^2$ and dried.

| Coating Solution for Spreading Layer: | |
|---|---|
| Water | 180 g |
| Imidazole | 4 g |
| Disodium creatine phosphate | 6 g |
| ADP | 2.4 g |
| AMP | 4 g |
| Disodium EDTA | 1.6 g |
| $MgCl_2.6H_2O$ | 4 g |
| Glucose | 2 g |
| $NAD^+$ | 2 g |
| N—acetylcysteine | 0.6 g |
| Diadenocine pentaphosphate | 80 mg |
| G6PDH | 30,000 U |
| Hexokinase | 40,000 U |
| Diaphorase | 30,000 U |
| Ascorbic acid oxidase | 30,000 U |
| Polyacrylamide (average molecular weight: 37,000; 20% aqueous solution) | 200 g |

The pH was adjusted to 6.5 by adding 2N HCl.

An analytical element for the determination of CPK activity of the present invention was prepared by the above method. 7% (w/v) human serum not containing CPK and 10 μl of administered serums determined to have CPK activities of 143, 490, 980 and 1894 U/l (37° C.) were each spotted onto the spreading layer of the analytical element and allowed to stand on a hot plate maintained at 37° C. in the state that evaporation of water was prevented. After two minutes and three minutes, the reflected optical density at a wavelength of 540 nm was measured. The results are shown in Table 1.

TABLE 1

| CPK Activity (U/l) | Reflected Optical Density 2 min. | 3 min. |
|---|---|---|
| 0 | 0.540 | 0.541 |
| 143 | 0.581 | 0.609 |
| 490 | 0.632 | 0.705 |
| 980 | 0.697 | 0.805 |
| 1894 | 0.787 | 0.944 |

As is apparent from the results of Table 1, according to an increase of CPK activity value, reflected optical density was increased to determine CPK activity using the element of the present invention.

COMPARATIVE EXAMPLE 1

An analytical element for the determination of CPK activity was prepared in the same manner as in Example 1 except that the amount of gelatin in the coating solution for a color forming layer was changed to 150 g. The amount of gelatin coated was about 20 g/m$^2$.

TEST EXAMPLE

Using the analytical elements of Example 1 and Comparative Example 1 which had been stored under the conditions shown in Table 2, the enzymatic activity of a commercially available administered serum having a CPK activity of about 80 U per liter was measured. The results are shown in Tables 2 and 3.

TABLE 2

CPK Activities Before and After Storage

| Storage Conditions | | Analytical Element | |
|---|---|---|---|
| Temperature (°C.) | Days | Example 1 | Comparative Example 1 |
| 4 | 0 | 79 | 79 |
| | 4 | 80 | 79 |
| | 7 | 78 | 77 |
| | 15 | 81 | 77 |
| | 21 | 82 | 77 |
| 45 | 0 | 79 | 79 |
| | 4 | 75 | 95 |
| | 7 | 75 | 84 |
| | 15 | 92 | 119 |
| | 21 | 94 | 136 |

TABLE 3

Activities measured Before and After Storage (Relative value with value measured with the analytical element of Example 1 stored at 4° C. for 0 days as 100)

| Storage Conditions | | Analytical Element | |
|---|---|---|---|
| Temperature (°C.) | Days | Example 1 | Comparative Example 1 |
| 4 | 0 | 100 | 100 |
| | 4 | 101 | 100 |
| | 7 | 99 | 97 |
| | 15 | 102 | 97 |
| | 21 | 104 | 97 |
| 45 | 0 | 100 | 100 |
| | 4 | 95 | 120 |
| | 7 | 95 | 134 |
| | 15 | 105 | 151 |
| | 21 | 119 | 172 |

From the above results, it can be seen that the analytical element of the present invention, even after being stored at high temperatures, is small in the error in determination of CPK activity as compared with that of Comparative Example 1.

While the invention has been described in detail and with reference to specific embodiments thereof, it will be apparent to one skilled in the art that various changes and modifications can be made therein without departing from the spirit and scope thereof.

What is claimed is:

1. In a dry analytical element for the determination of creatine kinase enzymatic activity, comprising at least one porous medium and at least one water permeable layer having a liquid contact relation with said porous medium, wherein said porous medium or said water permeable layer contains creatine phosphoric acid, ADP, a thiol compound as a creatine kinase activation agent, glucose, hexokinase, G6PDH, NAD$^+$, and an electron transmission agent, and a formazane dye forming tetrazolium salt, the improvement wherein said at least one water permeable layer contains a formazane dye forming tetrazolium salt and not more than 16 g/m$^2$ of gelatin.

2. In the dry analytical element as claimed in claim 1, the improvement wherein said element comprises, in sequence, at least one porous medium, at least one water permeable layer having a liquid contact relation with said porous medium, and a water impermeable light transmission support.

3. In the dry analytical element as claimed in claim 2, the improvement wherein one of the water permeable layers having a liquid contact relation with the porous medium contains a formazane dye forming tetrazolium salt.

4. In the dry analytical element as claimed in claim 1, the improvement wherein the thiol compound is N-acetylcysteine.

5. In the dry analytical element as claimed in claim 1, the improvement wherein the formazane dye forming tetrazolium salt is Nitrotetrazolium Blue.

6. In the dry analytical element as claimed in claim 1, the improvement wherein the mole ratio of the thiol compound to ADP is not more than 1.5:1.

7. In the dry analytical element as claimed in claim 1, the improvement wherein said electron transmission agent is selected from the group consisting of diaphorase, N-methylphenazinium, methosulfate and N-methoxyphenazinium methosulfate.

8. In the dry analytical element as claimed in claim 1, the improvement wherein said formazane dye forming tetrazolium salt is selected from the group consisting of 2-(p-iodophenyl)-3-(p-nitrophenyl)-5-phenyltetrazolium chloride; 3,3'-(3,3'-dimethoxy-4,4'-biphenylene)-bis[2,5-di-phenyltetrazolium chloride]; 3,3'-(4,4'-biphenylene)-bis[2,5-diphenyltetrazolium chloride]; and 3,3'-(3,3'-dimethoxy-4,4'-biphenylene)-bis[2-nitrophenyl)-5-phenyltetrazolium chloride].

9. In the dry analytical element as claimed in claim 1, the improvement wherein said thiol compound is selected from the group consisting of cysteine, glutathlone (reduced form), mercaptoethanol and N-acetylcystein.

* * * * *